United States Patent [19]

Leonard

[11] 4,292,254
[45] Sep. 29, 1981

[54] PREPARATION OF POLYISOCYANATES FROM POLYCARBAMATES

[75] Inventor: John J. Leonard, Springfield, Pa.

[73] Assignee: Atlantic Richfield Company, Los Angeles, Calif.

[21] Appl. No.: 197,848

[22] Filed: Oct. 17, 1980

[51] Int. Cl.$^3$ ................... C07C 118/00; C07C 125/07
[52] U.S. Cl. .................................. 260/453 P; 560/25
[58] Field of Search ...................... 260/453 P; 560/25

[56] References Cited

U.S. PATENT DOCUMENTS

| | | | |
|---|---|---|---|
| 2,946,768 | 7/1960 | Klauke et al. | 560/25 |
| 3,919,279 | 11/1975 | Rosenthal et al. | 260/453 P |
| 3,962,302 | 6/1976 | Rosenthal et al. | 260/453 P |
| 4,146,727 | 3/1979 | Shawl et al. | 560/25 |
| 4,162,362 | 7/1979 | Shawl | 560/25 |
| 4,172,948 | 10/1979 | Shawl | 560/25 |

Primary Examiner—Dolph H. Torrence
Attorney, Agent, or Firm—Delbert E. McCaslin

[57] ABSTRACT

In the process of producing polyisocyanates by
  (a) condensing an alkyl-N-phenylcarbamate having 1 to 3 carbons in the alkyl moiety in the presence of an acid to produce condensate containing diphenylmethane dicarbamates and polymethylene polyphenyl carbamates with by-product N-benzyl compounds, rearranging said N-benzyl compounds in said condensate with acid catalyst to obtain a pyrolysis feed mixture containing diphenylmethane dicarbamates and polymethylene polyphenyl carbamates,
  (b) thermally decomposing the carbamate moieties in the pyrolysis feed mixture to isocyanate moieties to produce polyisocyanates,
  the improvement comprises increasing the percent isocyanate content of said polyisocyanates by prior to step b) producing a solution by adding an organic cosolvent to the feed mixture, extracting that solution with an aqueous acid and removing the acid extract.

6 Claims, 1 Drawing Figure

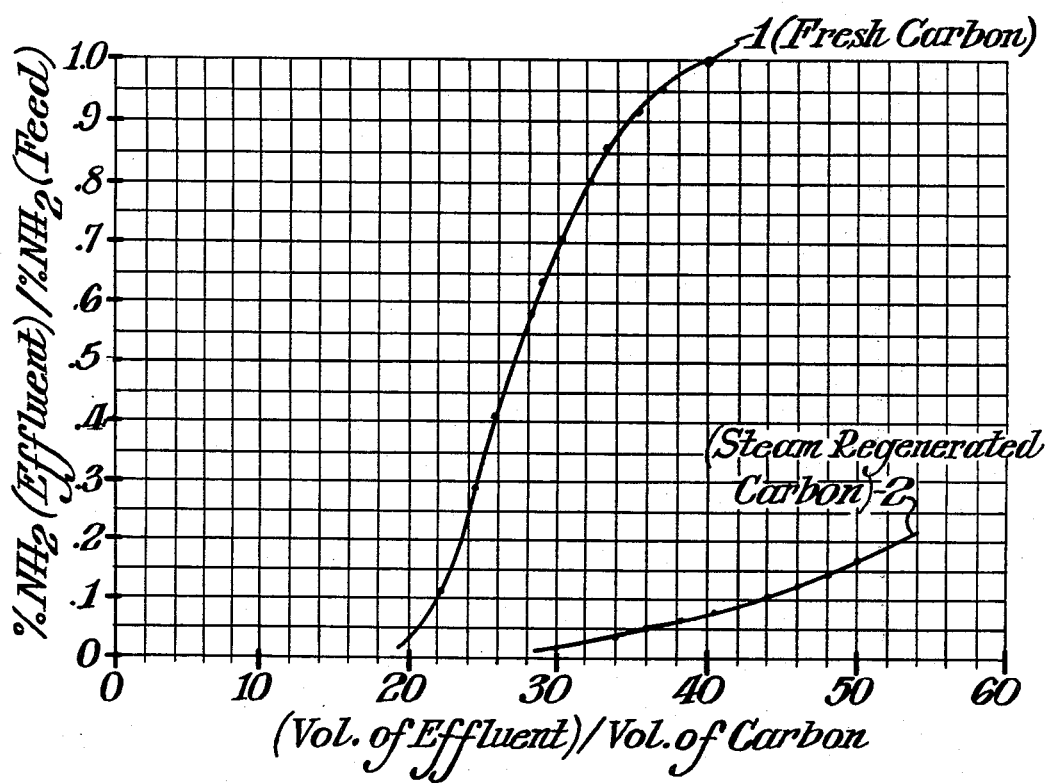

PREPARATION OF POLYISOCYANATES FROM POLYCARBAMATES

FIELD OF THE INVENTION

The present invention relates to an improvement in the process for the preparation of polyisocyanates from polycarbamates (polyurethanes). The improvement relates to removal of amine and amine salts from the polyurethane prior to its pyrolytic decomposition to polyisocyanate which results in higher levels of isocyanate content.

BACKGROUND OF THE INVENTION

Polymeric aromatic carbamic acid esters (polyurethanes) such as diphenylmethane dicarbamates and the related higher homologs, polymethylene polyphenyl carbamates, have become increasingly important products particularly, for use in the preparation of the commercially valuable diphenylmethane diisocyanates and mixtures of diisocyanates and the polyisocyanates by the decomposition of such polymeric aromatic carbamic acid esters in a suitable solvent as shown in Rosenthal et al., U.S. Pat. Nos. 3,962,302 and 3,919,279.

A proposed prior art process for the preparation of polymeric aromatic carbamic acid esters (polyurethanes) is disclosed in Klauke et al, U.S. Pat. No. 2,946,768 and involves the condensation of aryl carbamic acid esters with carbonyl compounds in a dilute aqueous acid condensation medium. However, in such process the carbonyl compound such as formaldehyde tends to react at the nitrogen of the carbamate to produce along with desired polyurethanes, varying amounts, i.e., generally between 15 percent and 50 percent by weight, of undesirable (alkoxycarbonyl)-phenylaminomethylphenyl compounds which includes the various dimers, trimers, tetramers, etc. of such compounds (also referred to herein as "N-benzyl" compounds). Attempts to prepare mono or diisocyanates and polyisocyanates or to otherwise use the mixture containing the undesired N-benzyl compounds, which cannot be converted to an isocyanate by pyrolysis, and polyurethanes presents many problems. However, the undesired N-benzyl compounds may be catalytically rearranged to a desired polyurethane in accordance with the teachings of Shawl et al, U.S. Pat. No. 4,146,727. Accordingly, a product mixture from a condensation as disclosed in aforementioned U.S. Pat. No. 2,946,768 containing diurethanes and polyurethanes, N-benzyl compounds, unreacted alkylphenylcarbamates and other by-products such as amines may be contacted at temperatures of from abour 50° C. to 170° C. with a protonic acid medium having a strength at least equal to a 75 percent sulfuric acid such as concentrated sulfuric acid or an acid medium comprising a Lewis acid having a concentration of at least 0.5 percent by weight based on the total reaction mixture, while maintaining a minimum amount of water in the system, to catalytically convert or rearrange said N-benzyl compounds.

Shawl, U.S. Pat. No. 4,172,948, discloses a similar rearrangement of N-benzyl compounds may be achieved by use of anhydrous hydrogen chloride under super atmospheric pressure.

Condensation of aryl carbamic acid esters with formaldehyde may also be conducted with organic sulfonic acids. Shawl, U.S. Pat. No. 4,162,362, teaches that condensation in the presence of an organic sulfonic acid essentially eliminates formation of N-benzyl compounds and suppresses certain other undesirable side reactions.

SUMMARY OF THE INVENTION

The acid catalyzed condensation of N-aryl carbamates and the acid rearrangement of N-benzyl compounds produce some hydrolysis of urethane groups to amino groups. Thus, for example, in the acid catalyzed condensation of ethyl-N-phenyl carbamate with formaldehyde some hydrolysis of the urethane (carbamate) groups occur and the amino compound would thus correspond to the carbamate from which it is derived. Such by-product amines have methylene bridged phenyl moieties with each phenyl having a carbamate or amino substituent.

By-product amino compounds may be present in the condensation-rearrangement product as free amines and as amine/acid salts. It has been discovered that when the by-product amines and amie salts accompany the condensation-rearrangement product to its pyrolytic decomposition to polyisocyanate, a significant detrimental effect results. For example, the amines and amine salts can react with isocyanate groups as they form to produce ureas or biurets. Additionally such undesirable ureas might at elevated temperatures catalyze isocyanate reactions to produce other unwanted by-products such as carbodiimides and isocyanurates.

The detrimental effect of the presence of amines in the pyrolytic production of polyisocyanates from corresponding polyurethanes is illustrated in Table I which shows that with reduced weight percent amino (as $NH_2$ groups) contained in the feed, a pyrolyzed product with increased weight percent isocyanate values (NCO groups) is obtained.

TABLE I

| Wt. % "$NH_2$" in Feed | Wt. % NCO in Pyrolysis Product |
|---|---|
| 0.005 | 31.3 |
| 0.01 | 31.0 |
| 0.02 | 30.8 |
| 0.03 | 30.5 |
| 0.04 | 30.3 |
| 0.05 | 30.1 |

Nitrobenzene is typically used as the solvent for condensation and rearrangement since it is highly polar yet unreactive in electrophylic reactions (benzene or toluene would condense with formaldehyde and are not suitable reaction solvents). It has been found that amine by-products may be acid extracted from a solution of the condensation-rearrangement product in a mixed solvent of nitrobenzene plus toluene or xylene. The amine compounds are extracted into the aqueous acid phase as salts and these salts may be removed from the aqueous acid by treatment with active carbon. The active carbon may be regenerated by conventional steam treatment.

Thus the present invention provides a method for increasing the percent isocyanate in a product of pyrolyzed polyurethane mixture by removing the undesirable amine and amine salts prior to pyrolysis. Removal of amine and amine salts can be achieved with an aqueous acid washing of the product of condensation and rearrangement of an N-aryl carbamate with formaldehyde. The amines are converted to the acid salts and separated from the condensation-rearrangement product along with the aqueous acid wash solution. The amine salts are then removed from the acid wash solution by contacting the solution with activated carbon prior to recycle for washing additional condensation-rearrangement product.

It is one object of this invention to provide a continuous process for removing amines from a solution containing polyurethanes by washing the polyurethane with an aqueous acid, separating the acid, contacting the acid with active carbon to remove amine salts and recycling the aqueous acid for washing additional polyurethane solution.

These and other objects and advantages of this invention will become apparent from the description of the invention which follows and from the claims.

BRIEF DESCRIPTION OF THE DRAWING

The FIGURE is a graph illustrating the effeciency of amine removal from an aqueous acid wash solution for both fresh carbon and steam regenerated carbon.

DESCRIPTION OF THE INVENTION

Condensation of alkyl-N-aryl carbamates with formaldehyde is known to yield polyfunctional carbamates with alternating methylene moieties and N-aryl carbamate moieties as shown by the formula

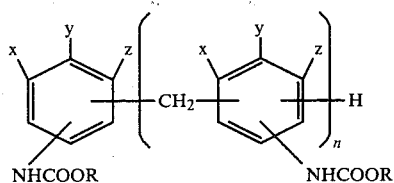

wherein x, y and z when the same are each hydrogen or when different x, y and z may be hydrogen, alkyl having 1–3 carbon atoms, —NHCOOR, —CH$_2$ArNHCOOR, or —N(COOR)CH$_2$Ar;

n is at least one;

R is alkyl having 1–3 carbon atoms and

Ar is phenyl which is unsubstituted or substituted with alkyl having 1–3 carbon atoms.

Production of polyfunctional carbamates by acidic condensation of monofunctional N-aryl carbamate with formaldehyde results in a small amount of the carbamate functional groups being hydrolyzed to amino groups as shown by the reaction

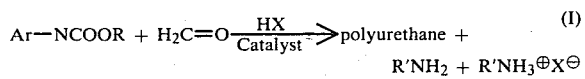

wherein Ar and R are as defined above, the polyfunctional carbamate is of formula (I), above, and R' is an organic moiety containing methylene bridged aromatic rings bearing carbamate or amino substituents. The amino by-products are not desirable and even though their presence is at low levels of concentration (usually in the range of 0.02 to 1.0 weight % amino) they have a significant detrimental effect of lowering the percentage isocyanate content when the polyfunctional carbamate is pyrolyzed to the corresponding polyisocyanate as shown in Table I, above.

In producing a condensation-rearrangement product from formaldehyde and an N-aryl carbamate, nitrobenzene is the usual solvent. The polyurethane condensate produced amounts to about 40–80% by weight in nitrobenzene. It has been discovered that the percentage isocyanate content in the pyrolyzed product can be increased by washing the polyurethane condensate-nitrobenzene solution with an aqueous acid prior to the pyrolysis. Suitable acids are methane-sulfonic acid, hydrochloric acid and sulfuric acid. The concentration of the acid can be 10 to 90 weight percent in water. Although the condensation-rearrangement product as a nitrobenzene solution may be directly treated with the aqueous acid, the preferred and more effective procedure is to add a cosolvent to the condensation-rearrangement product prior to the acid wash. Suitable cosolvents are toluene and xylene and suitable amounts of cosolvent are 1 to 90 percent by weight.

The phase ratio (i.e., the volume ratio of aqueous acid phase to organic solution being washed) ranges from 0.01 to 100 and the preferred range is 0.1 to 10. Suitable wash temperatures are from 0° C. to 100° C.

The condensation-rearrangement product solution is intimately contacted (e.g. by agitation) with the aqueous acid solution for a period of 1 to 60 minutes. An organic phase and an aqueous acidic phase are then separated and the amine salts extracted into the aqueous phase are removed from the aqueous phase by treatment with active carbon. The aqueous phase treated with active carbon to remove amine salts may then be recycled for use as the aqueous acid for washing further condensation-rearrangement. When the active carbon is spent, it may be regenerated by conventional steam treatment known for that purpose.

The following Examples are provided to illustrate the invention in accordance with the principles of this invention but are not to be construed as limiting the invention in any way except as indicated by the appended claims.

EXAMPLES 1–17 (Acid Washing Procedure)

In accordance with the teaching of U.S. Pat. No. 4,162,362 a condensate was prepared from ethyl-N-phenyl carbamate and formaldehyde catalyzed by methane sulfonic acid (CH$_3$SO$_3$H) in nitrobenzene solvent. The product nitrobenzene solution contained 40–80% by weight condensate and up to 1.0% by weight amine impurity.

For each of these Examples the condensate solution, cosolvent (toluene or xylene) and the aqueous acid solution (CH$_3$SO$_3$H or HCl) were charged to a three necked round bottom flask equipped with a stirrer, condenser, thermometer and bottom draw-off valve. The amounts of each component charges were adjusted to produce the desired aqueous to organic volume phase ratio. The contents of the flask were then vigorously stirred for 15 minutes at the desired temperature. Then the aqueous and organic phases were separated and analyzed for total amino groups by titration.

The precise data concerning the various parameters and conditions for each Example appear in the following Table II. Examples 1–6 indicate the need for a relatively concentrated aqueous acid. Examples, 1, 7 and 8–11 show the effect of temperature on wash effectiveness. Examples 8–11 also show the advantage of use of a cosolvent for the condensate solution.

TABLE II

| Run # | Temp. °C. | Acid (Wt. % in $H_2O$) | Phase[1] Ratio | Acid Estractions Cosolvent (Wt. % in Org. Phase) | # Washes[2] | % $NH_2$[3] Removal | $K_d$[4] |
|---|---|---|---|---|---|---|---|
| 1 | 25 | $CH_3SO_3H$ (75) | 1.0 | toluene (50) | 3 | 91 | 1.2 |
| 2 | 25 | $CH_3SO_3H$ (50) | 1.0 | toluene (50) | 2 | 61 | 0.6 |
| 3 | 25 | $CH_3SO_3H$ (50) | 0.1 | toluene (50) | 10 | 53 | .8 |
| 4 | 25 | $CH_3SO_3H$ (25) | 0.1 | toluene (50) | 10 | 20 | .2 |
| 5 | 25 | $CH_3SO_3H$ (5) | 0.1 | toluene (50) | 10 | 21 | .2 |
| 6 | 25 | $CH_3SO_3H$ (1) | 0.1 | toluene (50) | 10 | 1 | 0.06 |
| 7 | 50 | $CH_3SO_3H$ (50) | 1.0 | toluene (50) | 3 | 67 | .5 |
| 8 | 75 | $CH_3SO_3H$ (65) | .23 | toluene (52) | 1 | 73 | 11 |
| 9 | 75 | $CH_3SO_3H$ (65) | .36 | toluene (26) | 1 | 68 | 6 |
| 10 | 75 | $CH_3SO_3H$ (65) | .45 | toluene (10) | 1 | 53 | 3 |
| 11 | 75 | $CH_3SO_3H$ (65) | .52 | none | 1 | 50 | 2 |
| 12 | 25 | HCl (37) | 3.0 | toluene (50) | 2 | 80 | .4 |
| 13 | 25 | HCl (37) | 2.0 | toluene (50) | 2 | 76 | .5 |
| 14 | 25 | HCl (37) | 1.0 | toluene (50) | 2 | 65 | .3 |
| 15 | 25 | HCl (37) | 1.0 | Xylenes (50) | 1 | 44 | .8 |
| 16 | 25 | HCl (37) | 1.0 | Xylenes (50) | 2 | 63 | .6 |
| 17 | 25 | HCl (37) | 1.0 | Xylenes (50) | 3 | 80 | .8 |

[1] volume aqueous phase/volume organic phase
[2] number of washes at the indicated phase ratio
[3] based on $NH_2$ initially inorganic phase
[4] $K_d = \dfrac{\text{mole } NH_2/\text{l. aqueous phase}}{\text{mole } NH_2/\text{l. organic phase}}$ after each wash

EXAMPLE 18

Amine Salt Removal From Spent Acid (Carbon Treatment)

After washing the condensate solution, the separated aqueous acid phase contains salts of amines removed from the condensate solution. In order to recycle and reuse the aqueous acid, the amine salts must be removed. Applicants have discovered that active carbon is far superior to other adsorbants (e.g., clay, silica, polystyrene, etc.) for amine salt removal.

Calgon type "OL" carbon (20-50 mesh) was charged to a cylindrical glass column 15 inches high and 1.1 inches in diameter. Spent aqueous hydrochloric acid wash containing 0.01 weight percent total amino groups was passed through the carbon charged column and the column effluent monitored for total amine groups. The results are shown in the annexed figure as curve 1. When the carbon bed was saturated (about 40 volumes effluent/volume carbon) the carbon bed was water washed and treated with steam at 700°-800° C. to regenerate the carbon. Spent aqueous hydrochloric acid wash containing 0.01 weight percent total amino groups was passed through the steam regenerated carbon bed and as shown by curve 2. in the figure, steam regenerated carbon performed better than fresh carbon for removal of amine salt from aqueous hydrochloric acid wash.

What is claimed is:

1. In the process of producing polyisocyanates by
   (a) condensing an alkyl-N-phenylcarbamate having 1 to 3 carbons in the alkyl moiety in the presence of an acid to produce condensate containing diphenylmethane dicarbamates and polymethylene polyphenyl carbamates with by-product N-benzyl compounds, rearranging said N-benzyl compounds in said condensate with acid catalyst to obtain a pyrolysis feed mixture containing diphenylmethane dicarbamates and polymethylene polyphenyl carbamates,
   (b) thermally decomposing the carbamate moieties in the pyrolysis feed mixture to isocyanate moieties to produce polyisocyanates,
   the improvement comprises increasing the percent isocyanate content of said polyisocyanates by prior to step (b) producing a solution by adding an organic cosolvent to the feed mixture, extracting that solution with an aqueous acid and removing the acid extract.

2. The process according to claim 1 wherein the organic cosolvent is toluene or xylene.

3. The process according to claim 1 wherein the acid is hydrochloric acid, methane sulfonic acid or sulfuric acid.

4. The process according to claim 3 wherein the aqueous acid used for the extraction is a recycled acid extract from a previous extraction of a feed mixture/cosolvent solution which extract has been treated with active carbon prior to the recycle.

5. The process according to claim 4 wherein the active carbon is steam regenerated carbon.

6. The process according to claim 1 wherein the concentration of the aqueous acid is 10 to 90 weight percent in water.